United States Patent [19]

York et al.

[11] Patent Number: 5,192,780

[45] Date of Patent: Mar. 9, 1993

[54] METHODS USING ANTIALLERGICS AND ANTIHISTAMINES

[75] Inventors: Billie M. York, Fort Worth; Stella M. Robertson, Arlington; John M. Yanni, Burleson, all of Tex.

[73] Assignee: Alcon Laboratories, Inc., Fort Worth, Tex.

[21] Appl. No.: 734,728

[22] Filed: Jul. 23, 1991

Related U.S. Application Data

[63] Continuation-in-part of Ser. No. 616,049, Nov. 20, 1990, abandoned, which is a continuation-in-part of Ser. No. 452,189, Dec. 18, 1989, abandoned.

[51] Int. Cl.$^5$ .................. A61K 31/47; A61K 31/275
[52] U.S. Cl. .................................. 514/357; 514/522; 514/912
[58] Field of Search .................. 514/357, 522, 912

Primary Examiner—S. J. Friedman
Attorney, Agent, or Firm—Sally Yeager; James A. Arno

[57] ABSTRACT

Compositions of an antiallergic compound and an antihistamine for preventing and treating ophthalmic allergic responses are disclosed. Methods for preventing and treating ophthalmic allergic responses with the compositions are also disclosed.

4 Claims, No Drawings

METHODS USING ANTIALLERGICS AND ANTIHISTAMINES

This case is a continuation-in-part of U.S. Pat. Application No. 07/616,049 filed Nov. 20, 1990, which is a continuation-in-part of U.S. Pat. No. 452,189, filed on Dec. 18, 1989, both are abandoned.

SUMMARY OF THE INVENTION

This invention relates to compositions comprising an antiallergic compound and an antihistamine. The compositions are used to prevent allergic responses while also treating existing allergic conditions present in the eye. The invention is also directed to methods of preventing and treating allergic responses with the compositions.

BACKGROUND OF THE INVENTION

Antiallergics are compounds which prevent, inhibit or alleviate allergic reactions. It is believed that these compounds characteristically function as cell stabilizers and/or mast cell inhibitors preventing the usual degranulation of the mast cells in response to the presence of allergens. The eye, particularly the conjunctiva, has a relatively large number of mast cells. When allergens are present, they can bind to the immunoglobulin on the surface of these mast cells and trigger the breakdown, or what is known as the degranulation, of the cell. On degranulation, mast cell components, including histamines, are released into the environment outside the mast cell. Through a variety of mechanisms, these components can be responsible for symptoms associated with allergic responses such as itching, redness, lid swelling, vasodilation and chemosis.

Disodium cromoglycate (DSCG) has been used as an antiallergic to treat allergic conditions such as: vernal or allergic and chronic conjunctivitis (*Acta Ophthalmologica,* Vol.58, pp.121-124, 1980); vernal keratoconjunctivitis (*Current Eye Research,* Vol.2, No.11, 1982-83); and giant papillary conjunctivitis (*Arch. Ophthalmol.*-Vol.100, pp.1608-1610, 1982). DSCG has been reported as irritating to some patients (*Arch. Ophthalmol.,* Vol.100, No. 1, pp.412-413, 1982).

Cyano phenylene dioxamic compounds disclosed generally in U.S. Pat. No. 3,993,679 issued to Hall et al., and specifically for use as topical ophthalmic antiallergenics in U.S. patent application Ser. No. 312,434, both of which are incorporated herein by reference, are also antiallergic compounds useful in preventing allergic reactions resulting in mast cell degranulation. A species of the defined cyano phenylene dioxamic compounds of particular interest and representative thereof is N-N'-(2-chloro-5-cyano-m-phenylene)dioxamic acid and its pharmaceutically acceptable salts and esters, such as di-[tris (hydroxymethyl)methylammonium]-N-N'(2-chloro-5-cyano-m-phenylene)dioxamate also known as lodoxamide tromethamine, the active referred to herein as lodoxamide. Although the antiallergic, lodoxamide, is known to be efficacious in the treatment of allergic responses when topically applied to the eye, it can cause eye irritation and systemic side effects; see Watt et al., *J. Allergy Clin. Immunology,* Vol. 66, No.4 (1980).

Antihistamines are compounds which are administered to prevent histamines, released from mast cells in response to the presence of allergens, from binding to, for example, nerves and smooth muscle cells of the conjunctival blood vessels causing redness, itching and swelling. They serve to prevent or alleviate many of the symptoms which can result from degranulation of mast cells.

A combination of 4% DSCG and 0.2% of the antihistamine, chlorpheniramine maleate (Visuglican) has been used in patients with different forms of allergic conjunctivitis; see, Bonini et al., *Studies of Allergic Conjunctivitis,* Chibret Int'l J. of Ophth., Vol.5, No.2, 1987.

It is an object of the present invention to provide improved ophthalmic compositions comprising an antiallergic and an antihistamine, for treating existing symptoms of mast cell degranulation caused by the release of histamines and preventing further allergic and inflammatory symptoms by stabilizing the mast cells of the eye, or by inhibitng the allergic reaction which results in mast cell degranulation and ocular irritation.

It is a further object to provide methods for preventing and treating ophthalmic allergic conditions through administration of the disclosed compositions.

SUMMARY OF THE INVENTION

This invention is directed towards compositions for preventing and treating ophthalmic allergic responses comprising an antiallergic compound, such as lodoxamide, and an antihistamine such as pheniramine. The compositions prevent further allergic response as well as providing immediate relief of itchy, red and swollen eyes without producing significant side effects. The compositions are formulated as solutions, suspensions, gels or ointments for topical administration to the eye.

In addition, this invention is directed to methods for preventing and treating ophthalmic allergic responses using the compositions of antiallergics and antihistamines.

DETAILED DESCRIPTION OF PREFERRED EMBODIMENTS

The antiallergy compounds which are part of the compositions comprising an antiallergic and an antihistamine include any antiallergic that functions as a cell stabilizer and/or mast cell inhibitor; for example, cromolyn sodium (disodium salt of 1,3-bis(2-carboxychromon-5-yloxy)-2-hydroxypropane); lodoxamide (N,N'(2-chloro-5-cyano-m-phenylene)dioxamic acid), nedocromil (disodium 9-ethyl-6,9-dihydro-4,6-dioxo-10-propyl-4H-pyrano[3,2g]quinoline-2-8-dicarboxylate); and 6-methyl-N-(1H-tetrazol-5-yl)-2-pyridine carboxamide. In particular, antiallergics which can be used according to the present invention include the phenylene dioxamic compounds disclosed in U.S Pat. No. 3,993,679, particularly lodoxamide. Also, beta agonists can be used, such as albuterol/salbutamol (alpha$^1$-[[(1,1-dimethylethyl)amino]methyl]-4-hydroxy-1,3-benzenedimethanol; terbutaline(5-[2-[(1,1-dimethylethyl)amino]-1-hydroxyethyl]1,3-benzenediol;pirbuterolacetate (alpha$^6$ -[[1,1-dimethylethyl)amino]methyl]-3-hyroxy-2,6-pyridine-dimethanol monoacetate salt; fenotrol (5-[1-hydroxy-2-[[2-4-hydroxyphenyl)-1-methylethyl]amino]ethyl]-1,3-benzenediol; and bitolterol (4-methylbenzoic acid 4-[2-[(1,1,dimethylethyl)amino-1-hydroxyethy]-1,2-phenylene ester. The antiallergics can be used in compositions of the present invention at a concentration of about 0.01 to about 4.0 weight percent (wt. %), preferably 0.05 to 3.0 wt %.

Antihistamines which can be used in compositions of the present invention include all efficacious compounds in combination with the antiallergic compound. In addition, the antihistamines should not be uncomfortable upon installation in the eye and must be generally compatible in the common formulation environment of the antiallergic. Examples of antihistamines useful in the compositions of the present invention include, but are not limited to: 1-(2-ethoxyethyl)-2-(4-methyl-1-homopiperazinyl)-benzimidazole difumarate; levocabastine (−)-[3S-1(cis),3,4]]-1-[4-cyano-4-(4-fluorophenyl)cyclohexyl]-3-methyl-4-phenyl-4-piperidine-carboxylic acid monohydrochloride, (including the racemate, cabastine, and the isomer, dextrocabastne), mequitazine (10−(1-azabicyclo[2-2-2]oct-3-yl-methyl)-10H-phenothiazine; pheniramine (N,N, dimethyl gamma-phenyl-2-pyridinepropanamine); chlorpheniramine (gamma-(4-chlorophenyl)-N,N-dimethyl-2-pyridinepropanamine); brompheniramine (gama-(4-bromophenyl)-N,N-dimethyl-2-pyridine-propanamine); diphenhydramine (2-diphenylmethoxy-N,N-dimethylethanamine); hydroxyzine (2-[-2-[4-[(4-chlorophenyl)phenylmethyl]-1-piperazinyl]ethoxy]ethanol); astemizole (1-[(4-fluorophenyl)methyl]-N-[1-[2-(4-methylphenyl)ethyl]-4-piperidinyl]-1H-benzimidazol-2-amine); cetirizine ([2-[4-[(4-chlorophenyl)-phenylmethyl]-1-piperazinyl]ethoxy]acetic acid; terfenadine (alpha-[4-(1,1dimethylethyl)phenyl]-4-(hydroxydiphenylmethyl)-1-piperidinebutanol); rocastine (2-[2-(dimethylamino)ethyl]-2,3-dihydro-4-methyl-pyrido-[3,2-f]-1,4-oxazepine-5(4H)-thione(E)-2-butenedioate)]); loratadine (4-(8-chloro-5,6-dihydro-11H-benzo[5,6]cyclohepta[1,2-b]pyridin-11-ylidene)-1-piperidinecarboxylic acid ethyl ester); 5-[2-[4-bis(4-fluorophenyl)hydroxymethyl-1-piperidinyl]ethyl]-3-methyl]-2-oxazolidinone ethanedioate); pyrilamine (N-[(4-methoxyphenyl)methyl]-N',N'-dimethyl-N-2-[pyridinyl-1,2-ethanediamine); clemastine (2-[2-[1-(4-chlorophenyl)-1-phenylethoxy]ethyl]-1-methyl pyrrolidine). Compositions of the present invention preferably comprise pheniramine. The antihistamines will be present in the compositions at concentrations between about 0.01 and 3.0 wt. %., preferably 0.01-2% wt. %.

While antiallergics are known to be efficacious in the treatment of allergic responses when topically applied to the eye, they can cause side effects such as eye irritation and systemic side effects. In addition, antiallergics alone take considerable time, possibly days, to produce a significant clinical benefit. However, the compositions of the present invention, wherein the antiallergic is used in the presence of an antihistamine, can be sufficiently low so that efficacy is maintained while severe side effects are limited. The compositions also provide relatively rapid clinical results. Thus, with respect to the antiallergic combined with an antihistamine, unexpected results are achieved over the administration of an antiallergic or an antihistamine alone and over the sequential administration of these components.

The antiallergy compound and the antihistamine are formulated in compositions for topical application to the eye one to four times daily. As will be appreciated by those skilled in the art, the compositions can be formulated in various pharmaceutically acceptable forms for topical ophthalmic delivery including: solutions, suspensions, emulsions, gels, ointments and solid inserts, depending on the nature and characteristics of the antiallergics and antihistamines. The number of applications will depend upon a number of factors, including the discretion of a skilled clinician. Other factors include the concentration and effectiveness of the antiallergic and antihistamine being used and the vehicle used for their delivery. Compositions which are more viscous and, and/or provide for drug release over time, and/or which provide for better delivery to the areas of irritation will generally allow for less frequent application of the compositions.

In addition to the principle active ingredients, the compositions of the present invention may further comprise various formulatory ingredients, such as antimicrobial preservatives and tonicity agents. For example, antimicrobial preservatives include: benzalkonium chloride, thimerosal, chlorobutanol, methylparaben,propylparaben, phenylethylalcohol, EDTA, sorbic acid, POLYQUAD® and other agents equally well known to those skilled in the art. Such preservatives, if employed, will typically be used in an amount from about 0.0001 wt. % to 1.0 wt. %. Suitable agents which may be used to adjust tonicity or osmolality of the compositions include: sodium chloride, potassium chloride, mannitol, dextrose, glycerine and propylene glycol. If used, such agents will be employed in an amount of about 0.1 wt. % to 10.0 wt. %.

The preferred composition of the present invention comprises the antiallergic, lodoxamide, at concentrations between about 0.01 and 0.25 wt. %, preferably 0.1%; and the antihistamine, pheniramine, at concentrations of between about 0.05-0.35 wt. %., preferably about 0.2%. The composition is administered 4 times daily.

The following examples are illustrative of compositions of the present invention but are in no way limiting.

EXAMPLE 1

| Component | Concentration (% wt./vol.) |
| --- | --- |
| Pheniramine Maleate | 0.297 |
| Lodoxamide Tromethamine | 0.178 |
| Sodium Citrate.2H₂O | 0.0415 |
| Citric Acid.2H₂O | 0.0175 |
| Mannitol | 4.4 |
| Tyloxapol | 0.025 |
| Edetate Disodium | 0.01 |
| Benzalkonium Chloride | 0.007 + 5% excess |
| Hydroxypropylmethylcellulose (HPMC) | 0.38 |
| Sodium Hydroxide/Hydrochloric Acid | Adjust to pH 5.0 |
| Purified Water | q.s. 100 |

PREPARATION

A vessel was calibrated to 8L with a stir bar. 1,520 g of HPMC was then added to the vessel. Sixty percent of the purified water was added to another beaker and with stirring the following ingredients were added: 200 ml of 1.00% w/v tyloxapol; 58.8 ml of 1.00% w/v benzalkonium chloride; 3.32 g of sodium citrate 2H₂O; 1.40 g citric acid 2H₂O; 0.800 g edetate disodium; 23.76 g pheniramine maleate; 14.24 g lodoxamide tromethamine; and 352 g of mannitol. The pH was adjusted to 4.99 with 1N NaOH. The solution was then sterile filtered into the vessel containing the HPMC and brought to 100% volume with purified water.

EXAMPLE 2

| Component | w/v % |
| --- | --- |
| Lodoxamide Tromethamine | 0.15 |
| 1-(2-ethoxyethyl)-2-(4-methyl-1-homopiperazinyl)-benzimidazole difumarate | 0.1 |
| Sodium acetate | 0.1 |

-continued

| Component | w/v % |
| --- | --- |
| Acetic acid | 0.1 |
| Mannitol | 4.0 |
| Edetate Disodium | 0.01 |
| Benzalkonium Chloride | 0.01 + 5% excess |
| HCl/NaOH | Adjust to pH 5.0 |
| Purified Water | q.s. 100 |

EXAMPLE 3

| Component | w/v % |
| --- | --- |
| Lodoxamide Tromethamine | 0.178 |
| Levocabastine | 0.05 |
| Citric acid.2H$_2$O | 0.0175 |
| Sodium Citrate | 0.0415 |
| Sodium Chloride | 0.7 |
| Benzalkonium Chloride | 0.01 + 5% excess |
| Edetate Disodium | 0.01 |
| HCl/NaOH | Adjust to pH 5.0 |
| Purified Water | q.s. 100 |

EXAMPLE 4

| Ointment Formulation | |
| --- | --- |
| Component | w/v % |
| Lodoxamide Tromethamine | 0.175 |
| Astemizole | 0.5 |
| White petrolatum | q.s. 100 |
| Chlorobutanol | 0.5 + 5% excess |

EXAMPLE 5

| Suspension Formulation | |
| --- | --- |
| Component | w/v % |
| Lodoxamide Tromethamine | 0.350 |
| Terfenadine | 0.5 |
| Sodium Acetate | 0.1 |
| Acetic acid | 0.15 |
| Disodium edetate | 0.02 |
| Benzalkonium chloride | 0.01 + 5% excess |
| NaOH/HCl | Adjust to pH 5.5 |

-continued

| Suspension Formulation | |
| --- | --- |
| Component | w/v % |
| Purified Water | q.s. 100 |

EXAMPLE 6

| Component | w/v % |
| --- | --- |
| Lodoxamide Tromethamine | 0.350 |
| Loratadine | 0.5 |
| Citric acid.2H$_2$O | 0.0175 |
| Sodium Citrate.2H$_2$O | 0.415 |
| Mannitol | 4.X |
| Tyloxapol | 0.025 |
| Edetate Disodium | 0.01 |
| HCl/NaOH | Adjust to pH 5.0 |
| Benzalkonium Chloride | 0.01 + 5% excess |
| Purified Water | q.s. 100 |

This composition is administered 4 times daily.

We claim:

1. A pharmaceutical composition for treating ophthalmic allergic responses, comprising:
about 0.01 to about 4.0 wt. % of an antiallergic compound selected from the group consisting of lodoxamide, albuterol, terbutaline, pirbuterol acetate, fenotenol, and bitolterol and about 0.01 to about 3.0 wt. % of an anthistamine selected from the group consisting of 1-(2-ethyoxyethyl)-2-(4-methyl-1-homopiperazinyl)-benzimidazole difumerale (emedastine), levocabastine, and meguitazine.

2. The composition of claim 1 wherein the antiallergic compound is lodoxamide and the antihistamine is emedastine.

3. A method for treating opthalmic allergic responses, which comprises:
administering to the eye, a composition comprising about 0.01 to about 4.0 wt. % of an antiallergic compound selected from the group consisting of lodoxamide, albuterol, terbutaline, pipbuterol acetate, fenotenol, and bitolterol and about 0.1 to about 3.0 wt. % of an antihistamine selected from the group consisting of 1-(2-ethoxyethyl)-2-(4-methyl-1-homopiperazinyl)-benzimidazole difurmarale (emedastine), levocabastine, and meguitazine.

4. The method of claim 3 wherein the antiallergic compound is lodoxamide and the antihistamine is emedastine.

* * * * *